United States Patent
Fried

(10) Patent No.: US 12,280,084 B1
(45) Date of Patent: Apr. 22, 2025

(54) FENUGREEK FORMULATION FOR LOWERING BLOOD GLUCOSE AND WEIGHT LOSS

(71) Applicant: Robert Fried, New York, NY (US)

(72) Inventor: Robert Fried, New York, NY (US)

( * ) Notice: Subject to any disclaimer, the term of this patent is extended or adjusted under 35 U.S.C. 154(b) by 0 days.

(21) Appl. No.: 18/765,624

(22) Filed: Jul. 8, 2024

Related U.S. Application Data

(60) Provisional application No. 63/564,008, filed on Mar. 12, 2024.

(51) Int. Cl.
| | | |
|---|---|---|
| *A61K 36/48* | (2006.01) | |
| *A61K 31/12* | (2006.01) | |
| *A61K 33/24* | (2019.01) | |
| *A61P 3/04* | (2006.01) | |
| *A61P 3/10* | (2006.01) | |

(52) U.S. Cl.
CPC ............. *A61K 36/48* (2013.01); *A61K 31/12* (2013.01); *A61K 33/24* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 2015/0157672 A1* | 6/2015 | Cairns | A61K 36/38 424/730 |
| 2022/0401511 A1* | 12/2022 | Willis | A61K 36/87 |
| 2024/0041969 A1* | 2/2024 | Lundin | A23L 33/30 |

OTHER PUBLICATIONS

Chou et al (Scientific Reports, 7, 12265, 2017) (Year: 2017).*
King et al (Signal Transduction, 290(43), 26235-26248, 2015) (Year: 2015).*

* cited by examiner

*Primary Examiner* — Celeste A Roney
(74) *Attorney, Agent, or Firm* — Steven Yu; Ryuh Patent Law

(57) ABSTRACT

A therapeutic composition for treating a metabolic disorder such as chronic hyperglycemia or obesity. The therapeutic composition comprises fenugreek extract in a therapeutically effective amount sufficient to lower blood glucose or cause weight loss. The fenugreek extract may contain N-linoleoyl-2-amino-γ-butyrolactone. The therapeutic composition further comprises curcumin in a therapeutically effective amount sufficient to inhibit dipeptidyl-peptidase 4 (DPP4). The therapeutic composition further comprises chromium in a therapeutically effective amount sufficient to increase insulin sensitivity. Also disclosed is a therapeutic product (e.g. nutritional supplement) comprising the ingredients of the therapeutic composition in oral capsule form. Also disclosed is a method of treating a metabolic disorder.

14 Claims, 1 Drawing Sheet

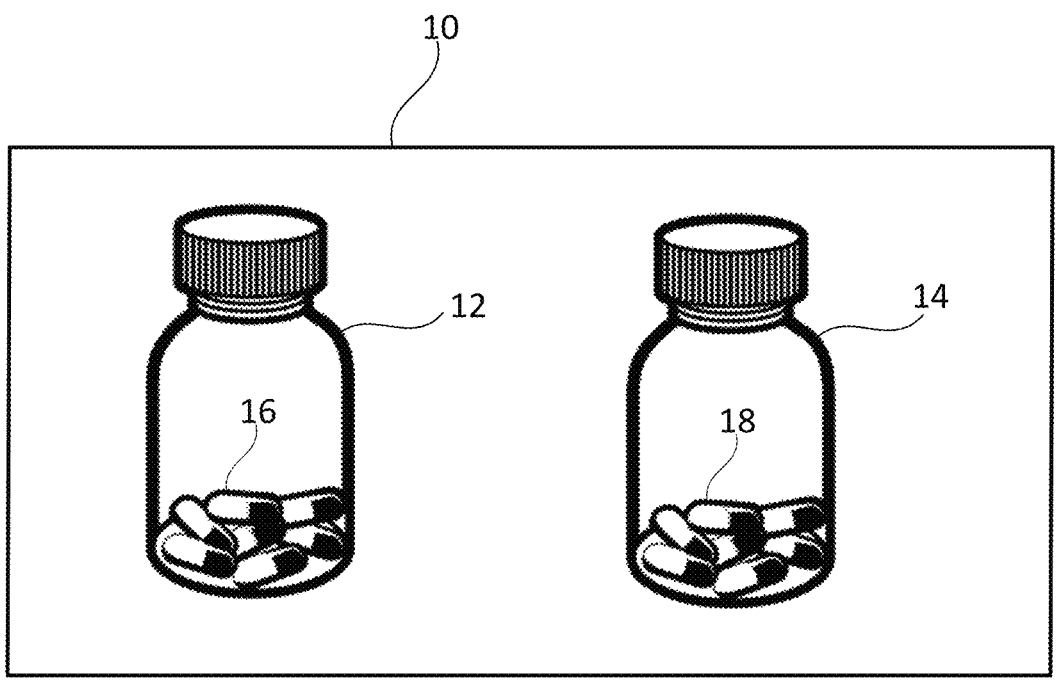

FENUGREEK FORMULATION FOR LOWERING BLOOD GLUCOSE AND WEIGHT LOSS

TECHNICAL FIELD

This invention relates to nutritional supplements for lowering blood glucose and weight loss.

BACKGROUND

GLP-1 (glucagon-like peptide-1) is a hormone produced by the intestines that plays a crucial role in metabolic regulation, such as regulating blood sugar levels. GLP-1 enhances sensitivity to insulin, which is a hormone responsible for regulating blood sugar levels. See Jiang Y et al., "GLP-1 Improves Adipocyte Insulin Sensitivity Following Induction of Endoplasmic Reticulum Stress." *Frontiers in Pharmacology* 2018; vol. 9. doi: 10.3389/fphar.2018.01168. Improved insulin sensitivity can promote weight loss and help prevent weight gain, particularly in patients with insulin resistance or type 2 diabetes.

In addition to its regulation of blood sugar levels, there are also other mechanisms by which GLP-1 can promote weight loss. The following is a summary of its role in weight loss. See Liu Y et al., "The Weight-loss Effect of GLP-1RAs Glucagon-Like Peptide-1 Receptor Agonists in Non-diabetic Individuals with Overweight or Obesity: A Systematic Review with Meta-Analysis and Trial Sequential Analysis of Randomized Controlled Trials." *Am J Clin Nutr.* 2023 September; 118 (3): 614-626. doi: 10.1016/j.ajcnut.2023.04.017. PMID: 37661106. GLP-1 works as an appetite suppressor. GLP-1 acts on the brain's appetite centers, increasing feelings of fullness and satiety. This leads to reduced food intake and calorie consumption, which can contribute to weight loss. Furthermore, GLP-1 slows down the rate at which the stomach empties its contents into the small intestine (i.e. slowed gastric emptying). See Marathe C S et al., "Effects of GLP-1 and incretin-based therapies on gastrointestinal motor function." *Exp Diabetes Res.* 2011; 2011:279530. doi: 10.1155/2011/279530. PMID: 21747825; PMCID: PMC3124003. This prolonged feeling of fullness can help reduce overall calorie intake.

Furthermore, GLP-1 inhibits the release of glucagon, a hormone that promotes the breakdown of stored fat and the release of glucose into the bloodstream. See Müller T D et al., "Glucagon-like peptide 1 (GLP-1)." *Mol Metab.* 2019 December; 30:72-130. doi: 10.1016/j.molmet.2019.09.010. PMID: 31767182; PMCID: PMC6812410. By reducing glucagon levels, GLP-1 can facilitate weight loss. Furthermore, GLP-1 reduces fat accumulation in various tissues, including the liver and adipose tissue, which can contribute to overall weight loss. See Liao C et al., "The effects of GLP-1 receptor agonists on visceral fat and liver ectopic fat in an adult population with or without diabetes and nonalcoholic fatty liver disease: A systematic review and meta-analysis." *PLOS One.* 2023 August; 18 (8): e0289616. doi: 10.1371/journal.pone.0289616. PMID: 37616255; PMCID: PMC10449217.

GLP-1-based therapies, such as GLP-1 agonists (e.g. liraglutide and semaglutide), have been approved for weight management for patients with obesity or overweight conditions. See Tzoulis P et al., "A Real-World Study of the Effectiveness and Safety of Semaglutide for Weight Loss." *Cureus.* 2024 May; 16 (5): e59558. doi: 10.7759/cureus.59558. These medications mimic the effects of GLP-1 and can lead to significant weight loss.

However, GLP-1 agonists have various problems and side effects. Whereas at lower doses, GLP-1 agonists promote insulin secretion and thereby lower blood sugar, higher doses are needed to achieve weight loss. At the relatively high doses required to achieve weight loss, GLP-1 agonists incur the risk of hypoglycemia. See Zhao Z et al., "Hypoglycemia following the use of glucagon-like peptide-1 receptor agonists: a real-world analysis of post-marketing surveillance data." *Ann Transl Med.* 2021 September; 9 (18): 1482. doi: 10.21037/atm-21-4162. PMID: 34734034; PMCID: PMC8506728. Also, GLP-1 agonists promote hyperplasia of the cells of the pancreas that line the smaller ducts. Shedding of these cells can obstruct the ducts, thereby provoking pancreatitis. See Sodhi M et al., "Risk of Gastrointestinal Adverse Events Associated With Glucagon-Like Peptide-1 Receptor Agonists for Weight Loss." *JAMA.* 2023 Nov. 14; 330 (18): 1795-1797. doi: 10.1001/jama.2023.19574. PMID: 37796527; PMCID: PMC10557026.

SUMMARY

In one aspect, this invention is a therapeutic composition for treating a metabolic disorder (see more details below). As used herein, the term "therapeutic" includes providing nutrition. As such, the therapeutic composition encompasses nutritional supplements. The therapeutic composition comprises fenugreek extract. The extract may be obtained from any suitable part of the fenugreek plant containing the GLP-1 potentiator called the "N55" compound (recently identified as N-linoleoyl-2-amino-γ-butyrolactone). Example plant parts from which the extract could be obtained include seeds, leaves, roots, flowers, etc. The therapeutic composition contains any therapeutically effective amount of fenugreek extract sufficient to lower blood glucose or cause weight loss. In some embodiments, each dose of the therapeutic composition contains 1,000-5,000 mg of fenugreek extract.

The therapeutic composition further comprises chromium (elemental). The chromium may be provided as any suitable pharmaceutical salt form such as chromium picolinate, chromium nicotinate, chromium polynicotinate, chromium chloride, or chromium histidinate. The therapeutic composition contains any therapeutically effective amount of chromium sufficient to increase insulin sensitivity. In some embodiments, each dose of the therapeutic composition contains 25-500 μg of chromium. The chromium amount specified herein means the amount of elemental chromium alone without accounting for the mass of the counterion(s).

The therapeutic composition further comprises curcumin. The therapeutic composition contains any therapeutically effective amount of curcumin sufficient to inhibit dipeptidyl-peptidase 4 (DPP4). In some embodiments, each dose of the therapeutic composition contains 1,000-5,000 mg of curcumin. As used herein, the term "dose" encompasses "serving". For example, one serving of the therapeutic composition is one dose thereof.

Therapeutic Product. In another aspect, this invention is a therapeutic product (e.g. nutritional supplement) comprising the various ingredients of the therapeutic composition in oral capsule form. In some embodiments, all the ingredients of the therapeutic composition are contained in one or more unit capsules. A single dose of the therapeutic composition may be provided in one or more capsules. For example, one dose of the therapeutic composition could be provided in a single capsule, or it may be divided into two capsules which are taken together.

However, there may be reasons to separate the ingredients of the therapeutic composition into different capsules. That is, the different ingredients may be separated in two or more different unit capsules. For example, a single conventional capsule may not be large enough to hold a sufficient amount of all the ingredients together.

The ingredients of the therapeutic composition may be separated in any suitable way. In some embodiments, the fenugreek extract is provided in one or more first unit capsules. The fenugreek extract could be in liquid form, such as aqueous solution, oil, emulsion, suspension, gel, etc. In such context, the first unit capsule (containing fenugreek extract) could be a softgel capsule. The curcumin is provided in one or more second unit capsules. The first unit capsule(s) or second unit capsule(s) may further comprise chromium. The amount of each of the ingredients contained in the capsules may be as described elsewhere herein.

In some embodiments, the therapeutic product comprises a first bottle containing a first set of capsules and a second bottle containing a second set of capsules. The therapeutic product could be a kit in which the first and second bottles are provided together in the same package. In some embodiments, each of the first set of capsules comprises fenugreek extract. Each of the second set of capsules comprises curcumin. The first or second set of capsules may further comprise chromium. The amount of each of the ingredients in the capsules may be as described elsewhere herein.

Treatment Method. In another aspect, this invention is a method of treating a metabolic disorder. Examples of such include obesity, dyslipidemia (e.g. hyperlipidemia), or chronic hyperglycemia (e.g. elevated blood sugar because of diabetes, insulin resistance, prediabetes, impaired glucose tolerance, etc.). As used herein, the term "treating" includes providing nutrition. As such, the method of treating encompasses giving nutritional benefits such as weight loss.

In some embodiments, the method of treatment comprises ingesting together a combination of ingredients that comprises fenugreek extract, chromium, and curcumin. As used in this context, "ingesting together" means ingesting the combination of ingredients simultaneously or near-simultaneously (within a time span of one minute). The user may ingest the dose amounts of each of the ingredients as described elsewhere herein. In some embodiments, the method of treatment comprises ingesting a capsule containing the therapeutic composition. For daily dosing, one or more capsules may be ingested per day.

The amount of fenugreek extract ingested is any therapeutically effective amount sufficient to lower blood glucose or cause weight loss. The amount of curcumin ingested is any therapeutically effective amount sufficient to inhibit dipeptidyl-peptidase 4 (DPP4). The amount of chromium ingested is any therapeutically effective amount sufficient to increase insulin sensitivity.

In some embodiments, the method of treatment comprises ingesting a first capsule and a second capsule (as explained above) together. For daily dosing, one or more of each of the first and second capsules may be ingested per day.

In some embodiments, the treatment is for a duration of at least 8 months; and in some cases, for at least 12 months. In some embodiments, wherein the metabolic disorder is obesity, the amount of weight loss is at least 7%; and in some cases, at least 10%.

BRIEF DESCRIPTION OF THE DRAWINGS

FIG. 1 shows an example of a therapeutic product kit of this invention.

DETAILED DESCRIPTION

Fenugreek (*Trigonella foenum-graecum*). Fenugreek is an herb that has been traditionally used for various purposes, including regulating blood sugar levels in the treatment of type-2 diabetes and weight loss in the treatment of obesity. Fenugreek improves overall glycemic control. See Kim J et al., "The effect of Fenugreek in Type 2 diabetes and prediabetes: A systematic review and meta-analysis of randomized controlled trials." *International Journal of Molecular Sciences*, September 12; 24 (18): 13999. doi: 10.3390/ijms241813999. Fenugreek can significantly reduce fasting blood glucose, 2 hour post-load glucose, and hemoglobin A1C. See Neelakantan N et al., "Effect of fenugreek (*Trigonella* foenum-*graecum* L.) intake on glycemia: a meta-analysis of clinical trials." *Nutrition Journal*, 2014 January; 13:7. doi: 10.1186/1475-2891-13-7. In regards to the mechanism of action on regulating blood glucose, fenugreek has been studied for its effects on glucagon-like peptide-1 (GLP-1), a hormone involved in regulating blood sugar levels and appetite. See Cortez-Navarrete M et al., "Role of Fenugreek, Cinnamon, *Curcuma longa*, Berberine and *Momordica charantia* in Type 2 Diabetes Mellitus Treatment: A Review." *Pharmaceuticals*. 2023; 16 (4): 515. doi: 10.3390/ph16040515.

Fenugreek has also been used for weight loss in the treatment of obesity. See Knott E J et al., "Fenugreek supplementation during high-fat feeding improves specific markers of metabolic health." *Sci Rep*. 2017 Oct. 6; 7 (1): 12770. doi: 10.1038/s41598-017-12846-x. PMID: 28986580; PMCID: PMC5630574. As explained above, GLP-1 works in weight loss through various effects, including suppressing hunger and inducing satiety, slowing gastric emptying, enhancing insulin secretion, and lowering blood glucose levels. See Liu Y et al., "The Weight-loss Effect of GLP-1RAs Glucagon-Like Peptide-1 Receptor Agonists in Non-diabetic Individuals with Overweight or Obesity: A Systematic Review with Meta-Analysis and Trial Sequential Analysis of Randomized Controlled Trials." *Am J Clin Nutr*. 2023 September; 118 (3): 614-626. doi: 10.1016/j.ajcnut.2023.04.017. PMID: 37661106.

Fenugreek seed extract contains an active compound called N55 (recently identified as N-linoleoyl-2-amino-γ-butyrolactone) that acts as a potentiator of GLP-1. See King K et al., "Isolation of Positive Modulator of Glucagon-like Peptide-1 Signaling from *Trigonella* foenum-*graecum* (Fenugreek) Seed." *J Biol Chem*. 2015 Oct. 23; 290 (43): 26235-48. doi: 10.1074/jbc.M115.672097. PMID: 26336108; PMCID: PMC4646272. Fenugreek also reduces systemic inflammation, which is linked to obesity and metabolic disorders. Fenugreek supplement suppliers generally suggest a dosage of 1-5 grams daily.

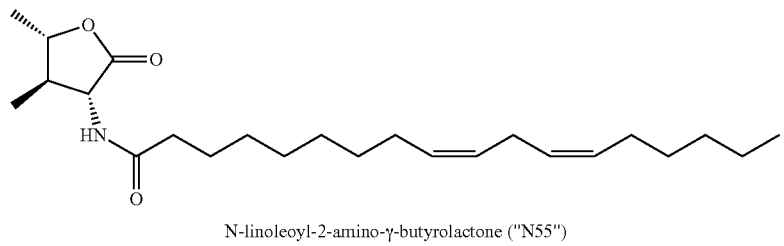 [SMILES: CCCCC/C=C\C/C=C\CCCCCCCC(=O)N[C@H]1C(=O)O[C@@H](C)[C@@H]1C]

N-linoleoyl-2-amino-γ-butyrolactone ("N55")

In some embodiments, the therapeutic composition contains 1,000-5,000 mg of fenugreek extract. In some embodiments, the oral capsule contains 300-2,500 mg of fenugreek extract (which, in some cases, could be administered in two daily doses). In some embodiments, the method of treatment comprises ingesting 1,000-5,000 mg of fenugreek extract.

Curcumin. In this invention, curcumin enhances the GLP-1 effect of fenugreek by reducing GLP-1 breakdown. In particular, dipeptidyl-peptidase 4 (DPP4) is an enzyme that cleaves and inactivates GLP-1. Curcumin inhibits the action of DDP4, which would otherwise break down GLP-1. See Cao W et al., "Identification of curcumin as a potential α-glucosidase and dipeptidyl-peptidase 4 inhibitor: Molecular docking study, in vitro and in vivo biological evaluation." *J Food Biochem.* 2022 March; 46 (3): e13686. doi: 10.1111/jfbc.13686. PMID: 33817806. By this inhibitory action, curcumin works to prolong the activity of GLP-1, thereby enhancing the effects of GLP-1. Thus, curcumin works synergistically with fenugreek's potentiation of GLP-1. Most publications suggest curcumin dosing at 500-2,000 mg per day. But other studies have shown that curcumin intake as high as 12 g/day over 3 months is safe and well-tolerated.

Curcumin has several other properties that contribute to weight loss and management of obesity through anti-inflammatory, antioxidant, and metabolic pathways. Curcumin promotes browning of white adipose tissue by inducing expression of β3AR (adrenergic receptor) and increasing norepinephrine levels, leading to increased fat burning. See Wang S et al., "Curcumin promotes browning of white adipose tissue in a norepinephrine-dependent way." *Biochem Biophys Res Commun.* 2015 Oct. 16; 466 (2): 247-53. doi: 10.1016/j.bbrc.2015.09.018. PMID: 26362189. Brown adipose tissue burns lipids to produce heat, thereby increasing energy expenditure and aiding weight loss.

Also, curcumin suppresses inflammation in adipose tissue by inhibiting macrophage infiltration, NF-κB activation, and inflammatory cytokines like TNF-α, MCP-1, and PAI-1. See Vari R et al., "Obesity-Associated Inflammation: Does Curcumin Exert a Beneficial Role?" *Nutrients.* 2021 Mar. 22; 13 (3): 1021. doi: 10.3390/nu13031021. PMID: 33809891; PMCID: PMC8004232. It also induces adiponectin secretion, which has anti-inflammatory effects. Also, curcumin inhibits adipocyte differentiation and promotes antioxidant activities in adipose tissue. Also, curcumin improves mitochondrial function in adipocytes, leading to better energy regulation and metabolism. See Zhao D et al., "Curcumin improves adipocytes browning and mitochondrial function in 3T3-L1 cells and obese rodent model." *R Soc Open Sci.* 2021 Mar. 17; 8 (3): 200974. doi: 10.1098/rsos.200974. PMID: 33959308; PMCID: PMC8074937.

In some embodiments, the therapeutic composition contains 1,000-5,000 mg of curcumin. In some embodiments, the oral capsule contains 300-2,500 mg of curcumin. In some embodiments, the method of treatment comprises ingesting 1,000-5,000 mg of curcumin.

Chromium. Chromium is an essential trace mineral that promotes weight loss through several possible mechanisms. Chromium stimulates insulin secretion, regulates glucose metabolism, and regulates fat metabolism. See Hua Y et al., "Molecular mechanisms of chromium in alleviating insulin resistance." *J Nutr Biochem.* 2012 April; 23 (4): 313-9. doi: 10.1016/j.jnutbio.2011.11.001. PMID: 22423897; PMCID: PMC3308119. Chromium enhances sensitivity to insulin and this makes glucose metabolism more efficient. This could lead to appetite suppression and aid in weight loss by reducing caloric intake. See Anton S D et al., "Effects of chromium picolinate on food intake and satiety." *Diabetes Technol Ther.* 2008 October; 10 (5): 405-12. doi: 10.1089/dia.2007.0292. PMID: 18715218; PMCID: PMC2753428. Chromium could also increase lean body mass (i.e. muscle) while reducing body fat. See Willoughby D et al., "Body composition changes in weight loss: strategies and supplementation for maintaining lean body mass, a brief review." *Nutrients*, vol. 10, no. 12 (2018): 1876. Chromium may have a mild effect on increasing metabolic rate, which could contribute to an increase in calorie burning.

Chromium can be taken as a dietary supplement (e.g. as chromium picolinate). Clinical studies have demonstrated that chromium supplementation can result in significant weight loss. The daily dose of chromium varies widely. For adults and teenagers, the recommended daily intake of chromium is 50-200 μg. However, larger doses of chromium are possible. In one study, up to 1,000 μg of chromium daily was used safely for up to six months. In another study, chromium was used safely in doses of 200-1,000 μg daily for up to two years. Supplements containing larger doses of chromium are available; most commonly providing 200-500 μg. However, some supplements contain even larger doses; up to 1 mg chromium (i.e. 1,000 μg).

In some embodiments, the therapeutic composition contains 25-750 μg of chromium. In some embodiments, the oral capsule contains 25-750 μg of chromium. In some embodiments, the method of treatment comprises ingesting 25-750 μg of chromium.

FIG. 1 shows an example therapeutic product kit of this invention. Kit 10 comprises a first bottle 12 and a second bottle 14 provided together in the same package. First bottle 12 contains capsules 16 comprising fenugreek extract. A single dose of fenugreek extract may be provided by one or more capsules 16. Capsules 16 may further comprise chromium. Second bottle 14 contains capsules 18 comprising curcumin. A single dose of curcumin may be provided by one or more capsules 18. Capsules 18 may further comprise chromium.

Experimental Trial

Clinical Case Example #1: An example therapeutic composition of this invention was tested for effect on weight loss. The subject was an 88 years old male with a body weight of about 250 lbs. and hemoglobin A1C of 7.6%. The subject started daily oral nutritional supplementation with the following: fenugreek seed extract (1,500 mg, twice daily), chromium picolinate (200 µg/day), and turmeric curcumin (1,000 mg/day). After about four months, the subject's body weight reduced to about 238 lbs. The subject continued the aforementioned nutritional supplementation. After about another six months (ten months total duration), the subject's body weight further reduced to about 233 lbs. and HgbA1C reduced to 6.9%. After about another four months (14 months total duration), the subject's body weight further reduced to about 222 lbs. and HgbA1C reduced to 6.6%. This represents a 28 lbs. (about 11%) weight loss over a duration of about 14 months.

Clinical Case Example #2: The therapeutic composition (i.e. fenugreek formulation) used in Clinical Case Example #1 above was also tested for efficacy on regulating blood glucose levels. The subject was a 79 year old woman, height of 5 feet 6 inches and with baseline a body weight of about 175 lbs. Despite long-term management of her type-2 diabetes with metformin, she still had blood glucose readings almost continuously in the low to high 200s mg/dl (e.g. 204, 228, 277) with hemoglobin A1C of 7.2%. A typical fasting blood sugar for her was 189.

Due to consistently high blood glucose levels, her endocrinologist prescribed Januvia (sitagliptin, a dipeptidyl peptidase-4 (DPP-4) inhibitor). Within just a few days of using Januvia, she developed diarrhea and signs of acute pancreatitis. She was told to stop the Januvia.

When sufficiently recovered from the pancreatitis, she started using the fenugreek formulation of this invention (combination of fenugreek, curcumin, and chromium picolinate) while she continued taking metformin. Within a few days of starting the fenugreek formulation, her blood glucose readings declined from well over 200 for most of the day, to around 180, with excursions into the mid-200s only after high-sugar meals (whereas prior to this regimen, her blood glucose was in the 200s at a steady state). Occasionally, while on the fenugreek formulation regimen, she had blood glucose readings down to 110. This was the first time in half a decade that the subject had readings as low as 110.

A few years earlier, her body weight had been as high as 250 lbs., but it was down to 195 lbs. at the time she began taking this fenugreek formulation regimen. Over the course of the three months while on this regimen, she has lost 20 pounds (down from about 195 lbs. to 175 lbs.), representing a 10.3% weigh loss in just three months' time, and without side effects. She tolerated this fenugreek formulation regime very well with no known episodes of hypoglycemia.

The foregoing description and examples merely illustrate the invention and are not intended to be limiting. Each of the disclosed aspects and embodiments of the invention may be considered individually or in combination with other aspects, embodiments, and variations of the invention. Also, unless otherwise specified, the steps of the methods of the invention are not limited to any particular order of performance. Persons skilled in the art may perceive modifications to these embodiments that incorporate the spirit and substance of the invention. Such modifications are within the scope of the invention.

Any use of the word "or" herein is intended to be inclusive and is equivalent to the expression "and/or," unless the context clearly indicates otherwise. As such, for example, the expression "A or B" means A, or B, or both A and B. Similarly, for example, the expression "A, B, or C" means A, or B, or C, or any combination thereof.

The terms "first, second, etc." with respect to elements may be used herein merely to distinguish one element from another element. Unless the context indicates otherwise, these are not intended to limit the elements regarding their composition or ordinal arrangement, such as defining the order, position, or priority of the elements.

The invention claimed is:

1. A method of treatment for a metabolic disorder, wherein the method comprises ingesting together multiple ingredients comprising:
    fenugreek extract in a therapeutically effective amount sufficient to lower blood glucose or cause weight loss;
    curcumin in a therapeutically effective amount sufficient to inhibit dipeptidyl-peptidase 4 (DPP4); and
    chromium in a therapeutically effective amount sufficient to increase insulin sensitivity;
    wherein the metabolic disorder is obesity and the treatment results in weight loss of at least 10%.

2. The method of claim 1, wherein the amount of fenugreek extract ingested is 1,000-5,000 mg.

3. The method of claim 1, wherein the amount of curcumin ingested is 1,000-5,000 mg.

4. The method of claim 1, wherein the amount of chromium ingested is 25-750 µg.

5. The method of claim 1, wherein the fenugreek extract contains N-linoleoyl-2-amino-γ-butyrolactone.

6. The method of claim 1, wherein the treatment is for a duration of at least 8 months.

7. The method of claim 1, wherein:
    the fenugreek extract is contained in a first set of one or more capsules;
    the curcumin is contained in a second set of one or more capsules.

8. The method of claim 7, wherein the chromium is contained in the first set of one or more capsules.

9. The method of claim 7, wherein the chromium is contained in the second set of one or more capsules.

10. The method of claim 7, wherein:
    the first set of one or more capsules is stored in a first bottle;
    the second set of one or more capsules is stored in a second bottle.

11. The method of claim 7, wherein the amount of fenugreek extract in each of the capsule(s) of the first set of capsules is 300-2,500 mg.

12. The method of claim 7, wherein the amount of curcumin in each of the capsule(s) of the second set of capsules is 300-2,500 mg.

13. The method of claim 8, wherein the amount of chromium in each of the capsule(s) of the first set of capsules is 25-750 µg.

14. The method of claim 9, wherein the amount of chromium in each of the capsule(s) of the second set of capsules is 25-750 µg.

* * * * *